(12) United States Patent
Okabe et al.

(10) Patent No.: US 8,232,365 B2
(45) Date of Patent: Jul. 31, 2012

(54) BIOMASS-DERIVED EPOXY COMPOUND AND MANUFACTURING METHOD THEREOF

(75) Inventors: Yoshiaki Okabe, Hitachi (JP); Hiroyuki Kagawa, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 203 days.

(21) Appl. No.: 12/645,726

(22) Filed: Dec. 23, 2009

(65) Prior Publication Data

US 2010/0155122 A1 Jun. 24, 2010

(30) Foreign Application Priority Data

Dec. 23, 2008 (JP) ................................. 2008-326634

(51) Int. Cl.
*C08G 59/06* (2006.01)
*C08G 59/02* (2006.01)
*C08G 59/04* (2006.01)

(52) U.S. Cl. ........................ 528/88; 528/366; 528/421

(58) Field of Classification Search .................... 528/88, 528/365, 366, 421
See application file for complete search history.

(56) References Cited

U.S. PATENT DOCUMENTS

| | | | | |
|---|---|---|---|---|
| 3,984,363 | A | * | 10/1976 | D'Alelio ...................... 526/270 |
| 4,001,202 | A | * | 1/1977 | Dilling et al. ................. 530/502 |
| 4,918,167 | A | * | 4/1990 | Glasser et al. ................ 530/502 |
| 2009/0281273 | A1 | | 11/2009 | Kurata |
| 2010/0006214 | A1 | | 1/2010 | Fujimaki et al. |

FOREIGN PATENT DOCUMENTS

| | | |
|---|---|---|
| JP | 09-235349 | 9/1997 |
| JP | 09-278904 | 10/1997 |
| JP | 2004-238539 | 8/2004 |
| JP | 2005-199209 | 7/2005 |
| JP | 2006-066237 | 3/2006 |
| JP | 2008-138061 | 6/2006 |
| JP | 2009263549 A * | 11/2009 |
| JP | 2009-286979 | 12/2009 |
| JP | 2009292884 A * | 12/2009 |
| WO | WO 2008/044556 | 4/2008 |

OTHER PUBLICATIONS

Machine translation of JP 2009292884 A, provided by the JPO website (no date).*
Machine translation of JP 2009263549 A, provided by the JPO website (no date).*
Machine translation of JP 2006066237 A, provided by the JPO website (no date).*
Machine translation of JP 2004238539 A, provided by the JPO website (no date).*
Advanced Technologies for Chemicals from Wood Resources, High Technology Information, CMC Publishing Co., Ltd., Tokyo, Japan, 2007, pp. 53-56 with translation.
Technologies for Higher Functionalities and for Recycling of Plant-Derived Plastics, Science & Technology Co., Ltd. Tokyo, Japan, 2007, pp. 129-131 with translation.
Henry Lee et al.; Epoxy Resins; McGraw-Hill Book Company, Inc.; New York 1960; pp. 2-3.
Japanese communication mailed on May 8, 2012, in connection with Japanese Application No. 2008-326634; 3 pages; Japanese Patent Office, Japan.

* cited by examiner

*Primary Examiner* — Michael J Feely
(74) *Attorney, Agent, or Firm* — Antonelli, Terry, Stout & Kraus, LLP.

(57) ABSTRACT

There is disclosed a biomass-derived epoxy compound as an epoxidized product of a raw-material biomass-derived compound having a weight-average molecular weight of 300 to 10000. The biomass-derived epoxy compound has a weight-average molecular weight of 600 to 20000 and is soluble in an organic solvent for the preparation of a varnish. The epoxy compound is prepared by dissolving the raw-material biomass-derived compound in an aqueous alkali solution; adding epichlorohydrin to the solution and heating the mixture; and evaporating epichlorohydrin from the heated mixture and precipitating a biomass-derived epoxy compound, in which the aqueous alkali solution has a pH of 13.5 to 11.0. The biomass-derived epoxy compound has both high solubility in organic solvents and satisfactory heat resistance and can be manufactured in a high yield on the basis of the raw material through a less number of processes.

4 Claims, 1 Drawing Sheet

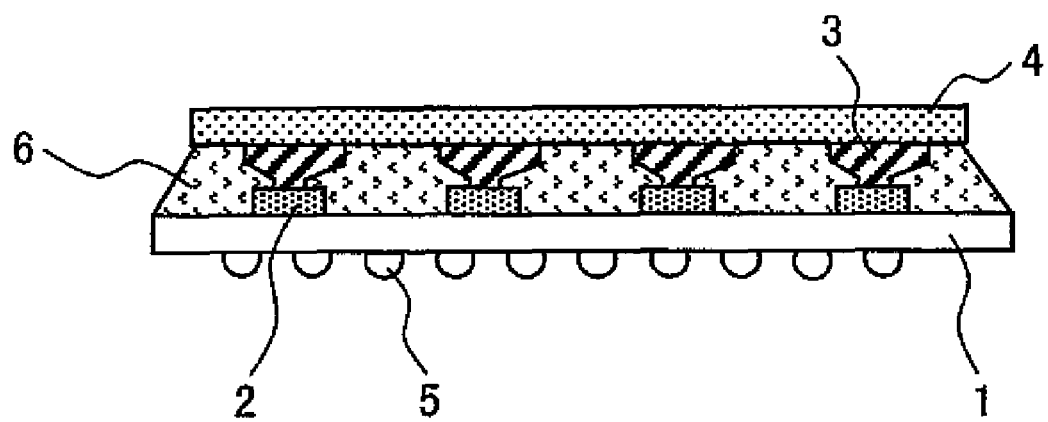

BIOMASS-DERIVED EPOXY COMPOUND AND MANUFACTURING METHOD THEREOF

CLAIM OF PRIORITY

The present application claims priority from Japanese Patent application serial No. 2008-326634, filed on Dec. 23, 2008, the content of which is hereby incorporated by reference into this application.

BACKGROUND OF THE INVENTION

1. Field of the Invention

The present invention relates to a biomass-derived epoxy compound and manufacturing method thereof.

2. Description of Related Art

From the viewpoint of carbon neutrality, vegetable- or plant-derived biomass has been expected as materials that do not cause global warming. The use of such plant-derived biomass has been attempted in resins, of which corn-derived thermoplastic poly(lactic acid)s have been mainly developed for practical use.

The use of such corn-derived thermoplastic poly(lactic acid)s, however, has not been spreading recently, because they suffer from resource conflict in the raw material corn with foodstuffs and they have low heatproof temperatures.

Accordingly, the current mainstream is to develop resins which use, as raw materials, "inedible resources" not conflicting with foodstuff and are highly resistant to heat. Among such inedible resources, ligneous wastes, i.e., unutilized trees, abound in Japan are expected as raw materials for biomass-derived resins.

Specifically, lignins have highly thermally stable polyphenol skeletons and are thereby expected to give biomass-derived thermosetting epoxy compounds, and these epoxy compounds in turn give epoxy resin compositions.

Lignins are plant-derived biomass and are firm or solid polymers containing propylphenols as backbone skeletons. Such lignins are classified by the process of extracting from trees typically as alkali lignins, Klason lignins, and steam explosion lignins.

Exemplary plant-derived biomass further includes lignophenols. The lignophenols have been prepared according to a technique of separating lignocellulose materials into lignophenol materials and carbohydrates (Patent Literature 1 (Japanese Patent Laid-open No. Hei 09-278904)). This technique utilizes a phase separation system developed by Prof. Masamitsu FUNAOKA (Mie University). As a result of the separation through the phase separation system, lignins are combined with phenols to give lignophenols. The resulting lignophenols are polyphenol resins that are linear molecules, have uniform structures, have a definite melting point of about 130° C., and are highly soluble.

To apply to various products, an epoxy resin composition should have satisfactory heat resistance properties and solubility. The solubility is required for the epoxy resin composition to be dissolved in an organic solvent to give a resin varnish, as described in Patent Literature 2 (Japanese Patent Laid-open No. Hei 09-235349). A prepreg is prepared by impregnating a base material with the resin varnish and drying the resulting article. Two or more plies of the prepreg are stacked, then thermally cured, and thereby yield products such as copper-clad laminates or insulating layers of motors. If a resin varnish contains an epoxy compound having insufficient solubility, it may often give a product unsatisfactory in properties such as heat resistance properties, because the ratio of the epoxy compound to a curing agent in the resin varnish may vary.

According to a known epoxidation process of a phenol compound, an epoxy compound having satisfactory solubility is prepared by adding an aqueous alkali metal solution to a solution of the phenol compound in epichlorohydrin and refluxing the resulting mixture (Non-Patent Literature 1 (H. Lee and K. Neville, "Handbook of Epoxy Resins", McGraw-Hill, New York, 1960 pp. 2-3)). However, when a biomass-derived phenol compound is epoxidized according to the known epoxidation process, the resulting epoxy compound is substantially insoluble in organic solvents.

This is probably because the raw material biomass has a complicated structure including a wide variety of groups such as hydroxyl group, carboxyl group, carbonyl group, aldehyde group, and styryl group; an alkali metal used in the known process acts upon these groups to cause cleavage and re-polymerization of the material compound to thereby give an epoxy compound having an increased molecular weight; and the increased molecular weight acts to reduce the solubility of the epoxy compound (Non-Patent Literature 2 ("Advanced Technologies for Chemicals from Wood Resources", CMC Publishing Co., Ltd., Tokyo Japan, 2007 pp. 53-56)).

The uses of epoxidized lignins as biomass-derived epoxy compounds are disclosed in Patent Literature 3 (Japanese Patent Laid-open No. 2005-199209) and Patent Literature 4 (Japanese Patent Laid-open No. 2006-066237).

Independently, the uses of epoxidized lignophenols as biomass-derived epoxy compounds are disclosed in Non-Patent Literature 3 ("Technologies for Higher Functionalities and for Recycling of Plant-derived Plastics" Science & Technology Co., Ltd., Tokyo Japan, 2007 pp. 129) and Patent Literature 5 (Japanese Patent Laid-open No. 2004-238539).

All these documents, however, fail to describe how to prevent biomass-derived epoxy compounds from increasing in molecular weight and how to allow them to have high solubility in organic solvents.

SUMMARY OF THE INVENTION

Epoxy resin compositions for the manufacturing of products each contain such an epoxy compound and a curing agent.

If lignins and lignophenols as biomass resources are epoxidized according to the known process, they give epoxy compounds having an increased molecular weight and thereby showing remarkably poor solubility in organic solvents. The biomass-derived resin compositions containing these epoxidized compounds and curing agents are difficult to be formulated into varnishes and, therefore, difficult to be applied to products.

Under these circumstances, we have made intensive investigations on the technique of controlling or specifying the molecular weight of a biomass-derived epoxy compound so that the biomass-derived epoxy compound can be readily formulated into a varnish. Even this technique, however, suffers from some problems. Typically, the yield of the biomass-derived epoxy compound is low relative to the material biomass, and the production of the biomass-derived epoxy compound needs a larger number of processes.

Accordingly, an object of the present invention is to provide a biomass-derived epoxy compound that has both high solubility and high heat resistance properties. Another object of the present invention is to provide a method that can manufacture the biomass-derived epoxy compound in a high yield on the basis of the raw material through a smaller number of processes.

Yet another object of the present invention is to provide, for example, an epoxy resin composition, such as a varnish, adhesive, or coating material, using the biomass-derived epoxy compound; a copper-clad laminate using them as a prepreg or insulating layer; and a motor product (electrical rotating machinery) using them.

Specifically, in an embodiment, the present invention provides a biomass-derived epoxy compound prepared through epoxidation of a raw-material biomass-derived compound having 300 to 10000 in a weight-average molecular weight, in which the biomass-derived epoxy compound after the epoxidation has 600 to 20000 in the weight-average molecular weight and is soluble in an organic solvent for preparing a varnish.

The biomass-derived epoxy compound according to the present invention has both high solubility in an organic solvent and satisfactory heat resistance properties and can be manufactured in a high yield on the basis of the raw material through a smaller number of processes.

BRIEF DESCRIPTION OF THE DRAWINGS

FIG. 1 is a schematic cross-sectional view illustrating a ball grid array according to an embodiment of the present invention.

DETAILED DESCRIPTION OF THE PREFERRED EMBODIMENTS

The present invention relates to biomass-derived epoxy compounds that are prepared from raw-material plant-derived biomass (biomass-derived compounds) and are highly soluble in organic solvents and to epoxy resin compositions which use the biomass-derived epoxy compounds and are highly thermally stable.

When biomass-derived epoxy compounds are prepared through epoxidation of raw-material lignins and lignophenols as biomass-derived compounds according to the known techniques, their molecular weights (weight-average molecular weights) are ten times as high as those of the raw materials. The biomass-derived epoxy compounds are thereby sparingly soluble in organic solvents. Biomass-derived epoxy resin compositions containing the biomass-derived epoxy compounds are difficult to be formulated into varnishes as solutions in organic solvents and therefore, difficult to be applied to products.

As is described above, the biomass-derived epoxy resin compositions prepared through epoxidation according to the known techniques have weight-average molecular weights ten times as high as those of the material compounds. To avoid problems caused by such high molecular weights, fractions having relatively high molecular weights have been separated and removed from the biomass-derived compounds, and only fractions having relatively low molecular weights have been used as raw materials. Accordingly, only very small portions of the biomass-derived compounds have been usable as raw materials.

In contrast, we have made investigations specifically to provide such a method for synthesizing (method for manufacturing) a biomass-derived epoxy compound as to achieve a ratio $Mw'/Mw$ of 2 or less, where $Mw'$ represents the weight-average molecular weight of a synthesized (epoxidized) biomass-derived epoxy compound; and $Mw$ represents the weight-average molecular weight of a raw-material biomass (biomass-derived compound).

In the investigations on the method, we have also made aim at not increasing the number of manufacturing processes and at providing a biomass-derived epoxy compound being highly soluble in organic solvents.

The present invention will be described in detail below.

The biomass-derived epoxy compound according to an embodiment of the present invention is prepared through epoxidation of a raw-material biomass-derived compound, has a weight-average molecular weight $Mw'$ of 600 to 20000, and is soluble in an organic solvent for the preparation of a varnish.

Exemplary biomass-derived compounds include lignins, lignophenols, soybean oils, and castor oils.

The weight-average molecular weight $Mw$ of the raw material biomass-derived compound before epoxidation preferably ranges from 300 to 10000. If a biomass-derived compound has a weight-average molecular weight $Mw$ less than 300, it may not give a biomass-derived epoxy compound having sufficiently high heat resistance properties, because such biomass-derived compound does not contain hydroxy group (OH group), aldehyde group (CHO group), and carboxyl group (COOH group) in a sufficient number. In contrast, if a biomass-derived compound has a weight-average molecular weight $Mw$ more than 10000, it may give a biomass-derived epoxy compound having a weight-average molecular weight $Mw'$ more than 20000 and being less soluble in organic solvents for the preparation of resin varnishes.

The weight-average molecular weight $Mw'$ is more preferably more than 1200 and 20000 or less, from the viewpoint of providing sufficient heat resistance properties and satisfactory solubility. It is furthermore preferably more than 12000 and 20000 or less, when high heat resistance properties are particularly needed.

An epoxy resin composition according to another embodiment of the present invention includes the biomass-derived epoxy compound and at least one curing agent.

The curing agent in the epoxy resin composition preferably includes a biomass-derived compound.

An epoxy resin varnish according to yet another embodiment of the present invention includes at least one organic solvent and the epoxy resin composition dissolved in the organic solvent, in which the epoxy resin composition is present at a concentration of 10 to 90 percent by weight.

The organic solvent in the epoxy resin varnish may be at least one selected typically from alcohols, carbonyl compounds, and aromatic compounds.

Exemplary alcohols for use in the epoxy resin varnish include 2-methoxyethanol, 2-ethoxyethanol, 2-propoxyethanol, and 2-butoxyethanol. Exemplary carbonyl compounds include methyl ethyl ketone, isobutyl ethyl ketone, cyclohexanone, γ-butyrolactone, and N,N-dimethylformamide; and exemplary aromatic compounds include toluene and xylenes.

A prepreg according to an embodiment of the present invention is prepared by impregnating a base material with the epoxy resin varnish and drying the resulting article.

The prepreg can be used for the manufacture typically of printed circuit boards, electronic devices and electrical rotating machineries.

A method for manufacturing a biomass-derived epoxy compound, according to an embodiment of the present invention, includes reacting a raw-material biomass-derived compound with epichlorohydrin in an aqueous alkali solution, in which the aqueous alkali solution has a pH of 13.5 to 11.0.

The aqueous alkali solution for use in the method may be selected typically from aqueous organic ammonium solutions, aqueous alkaline earth metal salt solutions and aqueous carbonate solutions.

Exemplary aqueous organic ammonium solutions include aqueous solutions of tetraalkylammonium hydroxides. Exemplary tetraalkylammonium hydroxides include tetramethylammonium hydroxide, tetraethylammonium hydroxide, tetrapropylammonium hydroxide, and tetrabutylammonium hydroxide. Each of different tetraalkylammonium hydroxides may be used alone or in combination.

Examples of the carbonates include sodium carbonate, potassium carbonate, and calcium carbonate.

The biomass-derived curing agents are compounds having hydroxy group (OH group), aldehyde group (CHO group), and/or carboxyl group (COOH group), and specific examples thereof include steam explosion low-molecular-weight lignins, alkali lignins, Klason lignins and lignophenols.

The weight-average molecular weight Mw before epoxidation preferably ranges from 300 to 10000. If a material biomass-derived compound has a weight-average molecular weight Mw less than 300, it may contain OH group, CHO group and carboxyl group in insufficient numbers and may thereby give a biomass-derived epoxy compound having unsatisfactory heat resistance properties. In contrast, if a material biomass-derived compound has a weight-average molecular weight Mw more than 10000, it may give a biomass-derived epoxy compound having insufficient solubility in organic solvents through epoxidation.

The weight-average molecular weight Mw is more preferably more than 1200 and 10000 or less from the viewpoint of providing sufficient heat resistance properties and satisfactory solubility.

If a varnish contains an undissolved epoxy resin composition (undissolved biomass-derived epoxy compound), the ratio of the biomass-derived epoxy compound to the curing agent partially deviates from the stoichiometric ratio, and this may cause a cured article prepared from the varnish to be unsatisfactory in properties such as heat resistance properties, stability, and resistance to water absorption (water-blocking properties). Therefore, the biomass-derived epoxy compound should be soluble in an organic solvent for the preparation of a varnish.

Petroleum-derived epoxy compounds and petroleum-derived curing agents have definite chemical structures. The epoxy resin composition further containing these epoxy compounds and/or curing agents can control its properties easily. In addition, most of such petroleum-derived epoxy compounds and petroleum-derived curing agents are satisfactorily soluble in organic solvents.

Petroleum-derived epoxy compounds and petroleum-derived curing agents for use herein preferably have satisfactory solubility and sufficient heat resistance properties. Specific examples of petroleum-derived epoxy compounds include bisphenol-A epoxy compounds, bisphenol-F glycidyl ether epoxy compounds, bisphenol-S glycidyl ether epoxy compounds, bisphenol-AD glycidyl ether epoxy compounds, phenol-novolac epoxy compounds, cresol-novolac epoxy compounds, and 3,3',5,5'-tetramethyl-4,4'-dihydroxybiphenylglycidyl ether epoxy compounds although they are not limited to the above compounds. The epoxy compounds preferably contain minimum amounts of ionic substances such as $Na^+$ and $Cl^-$.

Exemplary petroleum-derived curing agents for use herein include amines with linear structure, alicyclic amines, aromatic amines, other amines with cyclic structure, modified amines, acid anhydrides (e.g., maleic anhydride), polyhydric phenol curing agents, bisphenol curing agents, polyphenol curing agents, novolac phenol curing agents, and alkylene-modified phenol curing agents. Each of different petroleum-derived curing agents may be used alone or in combination. The curing agents preferably contain minimum amounts of ionic substances such as $Na^+$ and $Cl^-$.

Where necessary, the epoxy resin composition may further contain one or more of known curing accelerators generally used as catalysts. Each of the different catalysts (curing accelerators) can be used alone or in combination. Exemplary curing accelerators include tertiary amine compounds, imidazoles, organic sulfines, phosphorus compounds, salts of tetraphenylboron, and derivatives of them. The amount of curing accelerators is not especially limited, as long as being such an amount as to exhibit a curing-accelerating activity.

Where necessary, the epoxy resin composition may further contain one or more of known coupling agents. Each of the different coupling agents may be used alone or in combination. Exemplary coupling agents include epoxysilanes, aminosilanes, ureidosilanes, vinylsilanes, alkylsilanes, organic titanates, and aluminum alkylates.

The epoxy resin composition may further contain one or more flame retardants. Exemplary flame retardants include phosphorus-containing compounds (including elementary phosphorus), such as red phosphorus (amorphous phosphorus), phosphoric acid and phosphoric acid esters; nitrogen-containing compounds such as melamines, melamine derivatives, triazine-ring-containing compounds, cyanuric acid derivatives and isocyanuric acid derivatives; phosphorus-nitrogen-containing compounds such as cyclophosphazenes; metallic compounds such as zinc oxide, iron oxide, molybdenum oxide and ferrocene; antimony oxides such as antimony trioxide, antimony tetroxide and antimony pentaoxide; and brominated epoxy resins. Each of different flame retardants may be used alone or in combination.

The epoxy resin composition may further contain one or more inorganic fillers generally used. Such inorganic fillers are used for the purpose typically of improving properties such as hygroscopicity (moisture absorption), thermal conductivity and strength, and/or reducing coefficient of thermal expansion. Exemplary fillers include powdery substances typically of fused silica, crystalline silica, alumina, zircon, calcium silicate, calcium carbonate, potassium titanate, silicon carbide, silicon nitride, aluminum nitride, boron nitride, beryllia (beryllium oxide), zirconia, zircon, fosterite, steatite, spinel, mullite, and titania; beads prepared from these powders; and glass fibers.

Exemplary inorganic fillers having flame retardancy further include aluminum hydroxide, magnesium hydroxide, zinc silicate, zinc molybdate and the like. Each of different inorganic fillers may be used alone or in combination.

The epoxy resin composition may further contain one or more other resins, one or more catalysts for the acceleration of reaction and/or one or more additives according to necessity. Exemplary additives include flame retardants, leveling agents and defoaming agents.

The epoxy resin composition may further contain one or more ion trappers (ion scavengers) for improving properties of product electronic devices, such as moisture resistance and properties at high temperature (heat resistance properties). The ion trappers for use herein are not especially limited in their type, and can be any of known ion trappers or ion scavengers. Exemplary ion trappers include hydrotalcites; and hydrous oxides of elements such as magnesium, aluminum, titanium, zirconium and bismuth. Each of different ion trappers may be used alone or in combination.

The epoxy resin composition may further contain other additives according to necessity. Exemplary other additives herein include stress-relaxing agents such as silicone rubber powders; colorants such as dyestuffs and carbon blacks; leveling agents; and defoaming agents.

The epoxy resin composition may be prepared by mixing components (materials) according to any process or device, as long as the components (materials) can be uniformly dispersed in and mixed with one another. In general, the composition is prepared by weighing predetermined amounts of the materials, and dispersing and mixing them with one another typically using a device such as ball mill, triple roll mill, vacuum masher, pot mill or hybrid mixer.

The epoxy resin composition containing the biomass-derived epoxy compound as a component shows high solubility in organic solvents and satisfactory heat resistance properties and can thereby give products with remarkably improved reliability.

When used in the preparation of a copper-clad laminate, the epoxy resin composition should be dissolved in a solvent (organic solvent), because the preparation essentially includes a step of impregnating a glass cloth with a varnish of the epoxy resin composition.

The epoxy resin composition is also satisfactorily formable (moldable) by hot forming. Typically, when an epoxy resin composition is formulated into an encapsulant, and the encapsulant is charged into gaps (100 μm gaps) in a flip-chip packaged ball grid array (FC-BGA) according to a capillary flow method, if the epoxy resin composition has insufficient formability, it may cause encapsulation failure at corner edges of the chip and bubble entrainment, and this may lead to deterioration in reliability of the resulting semiconductor device.

Exemplary products in which the epoxy resin composition is used include copper-clad laminates each using a prepreg prepared from the epoxy resin composition; computers and cellular phones including the copper-clad laminates; motors whose coil unit is insulated by the prepreg; and industrial robots and rotating machineries including the motors. Exemplary products further include chip-size packages in which devices are encapsulated with the encapsulant using the epoxy resin composition; and adhesives and coating materials (paints) using the biomass-derived epoxy resin composition.

The present invention will be illustrated in further detail with reference to several examples and comparative examples below. It should be noted, however, that these examples are never construed to limit the scope of the present invention.

Test materials used in the examples are shown below by a trade name or abbreviation.

Low-molecular-weight lignin: Lignin derived from raw-material Cedar lignin, having a weight-average molecular weight Mw of 1500, and having a hydroxyl equivalent of 400 g/eq Lignophenol: One having a weight-average molecular weight Mw of 4400 and having a hydroxyl equivalent of 160 g/eq (supplied by TOYO JUSHI CORPORATION)

HP 850: o-Cresol-novolac resin having an epoxy equivalent of 106 g/eq (supplied by Hitachi Chemical Co., Ltd.)

P-200: Imidazole curing catalyst (supplied by Japan Epoxy Resins Co., Ltd.)

KBM 403: Coupling agent (γ-glycidoxypropyltrimethoxysilane; supplied by Shin-Etsu Chemical Co., Ltd.)

JER 828: Bisphenol-A epoxy resin, having an epoxy equivalent of 190 g/eq (supplied by Japan Epoxy Resins Co., Ltd.)

RE 404S: Bisphenol-F epoxy resin, having an epoxy equivalent of 165 g/eq (supplied by Nippon Kayaku Co., Ltd.)

KAYAHARD AA: 4,4'-Methylenebis(2-ethylaniline) (supplied by Nippon Kayaku Co., Ltd.)

MHAC-P: Methyl-3,6-endomethylene-1,2,3,6-tetrahydrophthalic anhydride, having a weight-average molecular weight Mw of 178 (supplied by Hitachi Chemical Co., Ltd.)

Tests were conducted according to the following methods.
Test Methods
(a) Solubility The solubility of a sample epoxidized biomass (biomass-derived epoxy compound) was tested by visually observing how the biomass-derived epoxy compound was dissolved at a concentration of 50 percent by weight in a 1:1 (by weight) solvent mixture of 2-methoxyethanol and methyl ethyl ketone. A sample fully dissolved in the solvent mixture was evaluated as having good solubility (Good), and one partially insoluble in the solvent mixture was evaluated as having poor solubility (Poor).

(b) Weight-Average Molecular Weight

The weight-average molecular weight (in terms of polystyrene) of a sample was measured using the detector Model L-4000 (UV detector; 270 nm) supplied by Hitachi Chemical Co., Ltd. under the following conditions:

Column: Two Gelpak GL-S300MDT-5 columns
Column temperature: 30° C.
Flow rate: 1.0 mL per minute
Eluent: DMF/THF=1/1 (1) plus 0.06 M phosphoric acid plus 0.06 M LiBr, wherein DMF represents N,N-dimethylformamide; and THF represents tetrahydrofuran.

(c) Epoxy Equivalent

The epoxy equivalent of a sample was measured in accordance with the method specified in Japanese Industrial Standards (JIS) K 7236 (the pyridine hydrochloride method).

(d) Hydroxyl Equivalent

The hydroxyl equivalent of a sample was measured in accordance with the method specified in JIS K 6755.

(e) Detection of Epoxidation

The $^1$H-NMR spectrum of a sample epoxidized product (biomass-derived epoxy compound) was measured using deuterated dimethyl sulfoxide as a solvent, and the presence of protons derived from introduced epoxy group was detected from peaks at 2.6 ppm and 2.8 ppm. In addition, the presence of epoxy group was further detected from the presence of an absorption at 910 cm$^{-1}$ in a Fourier transform infrared spectroscopy (FT-IR).

(f) Glass Transition Temperature (Tg)

The glass transition temperature (Tg) of a sample was determined in the following manner. Each of the compositions according to Examples 5 to 11 and Comparative Example 5 as given in Table 1 was cured at temperatures ranging from room temperature to 250° C. for one hour to give a film 100 μm thick. The storage modulus E' and loss modulus E" of the film were measured using a dynamic mechanical analyzer (DMA) while raising the temperature at a rate of 5° C. per minute, from which tangent delta (tan δ was determined as the ratio of the loss modulus E" to the storage modulus E', and the glass transition temperature (Tg) was determined from the peak temperature of tan δ.

(g) Shear Strength

A cured article (as a block) having a length of 4 mm, a width of 4 mm and a thickness of 1 mm was formed from a sample epoxy resin on a substrate made of a negative-working photosensitive polyimide (supplied by HD MicroSystems, Ltd., under the trade name PL-H708); the adhesive strength under shear (longitudinal shear strength) between the photo-sensitive polyimide and the epoxy resin cured article was measured using the Multi-purpose Bondtester (Dage, Model PC 2400) to evaluate adhesive properties. In the measurement, a shearing tool was fixed 50 μm above the photosensitive polyimide substrate, and the shear strength was measured at a tool speed of 300 μm per second.

(h) Resistance to Soldering Heat

The resistance of a sample copper-clad laminate to soldering heat (heat applied upon soldering) was measured in accordance with the test method specified in JIS C 6481. Specifically, according to the test method, a sample copper-clad laminate 50 mm thick was prepared, the copper clad was etched, the resulting article was placed in boiling distilled water for one hour to absorb water and was immersed in a bath of molten solder at 260° C. for three minutes, and whether peeling occurred or not was determined.

(i) Volume Resistivity

The volume resistivity of a sample was measured in accordance with JIS C 6481 at 25° C.

(j) Peel Strength

The peel strength of the copper clad was measured in accordance with JIS C 6481.

Some examples will be described below.

EXAMPLE 1

In a 2-liter four-neck flask equipped with stirring blades, a condenser and a thermometer were placed 100 grams of a low-molecular-weight lignin and 300 grams of a 10% aqueous tetramethylammonium hydroxide solution, followed by stirring for 30 minutes to give a solution.

The solution was further combined with 300 grams of epichlorohydrin, and the mixture was heated under reflux on an oil bath at 120° C. for one hour. The reaction mixture was cooled to room temperature, placed in a separating funnel, and washed with pure water until the oil layer became neutral.

After removing water therefrom, the residue was combined with 50 grams of a 20% aqueous tetramethylammonium hydroxide solution and heated under reflux at 120° C. for one hour, followed by washing with water.

This was placed in a rotary evaporator, from which about 80% of epichlorohydrin, water and by-products were evaporated and removed, the residue was placed in 2 liters of ethyl alcohol and thereby yielded white precipitates.

Ethyl alcohol was used herein, but another alcohol such as methyl alcohol, propyl alcohol, butyl alcohol, pentyl alcohol or hexyl alcohol may be used.

The precipitates were collected by filtration, dried in vacuo, and thereby yielded an epoxidized low-molecular-weight lignin EL1.

The epoxidized low-molecular-weight lignin EL1 gave peaks at 2.6 ppm and 2.8 ppm through proton nuclear magnetic resonance spectroscopy ($^1$H-NMR) and gave an absorption at 914 cm$^{-1}$ through FT-IR, verifying that epoxy groups have been introduced (added) to lignin.

The epoxidized low-molecular-weight lignin EL1 according to this example was prepared in a yield of 106 grams and had a weight-average molecular weight Mw' of 2800. This was satisfactorily dissolved in an equivalent weight of 2-methoxyethanol (2MOE). The aqueous tetramethylammonium hydroxide solution had a pH of 12.9. As used herein "pH" refers to a hydrogen ion concentration.

EXAMPLE 2

An epoxidized low-molecular-weight lignin EL2 was prepared through synthesis by the procedure of Example 1, except for using an aqueous tetraethylammonium hydroxide solution having a pH of 12.6. EL2 was prepared in a yield of 104 grams, had a weight-average molecular weight Mw' of 2590, and was soluble in 2MOE. The introduction of epoxy groups into lignin was confirmed through $^1$H-NMR and FT-IR analyses.

EXAMPLE 3

An epoxidized low-molecular-weight lignin EL3 was prepared through synthesis by the procedure of Example 1, except for using an aqueous potassium carbonate solution having a pH of 11.6. EL3 was prepared in a yield of 110 grams, had a weight-average molecular weight Mw' of 2900, and was soluble in 2MOE. The introduction of epoxy groups into lignin was confirmed through $^1$H-NMR and FT-IR analyses.

EXAMPLE 4

An epoxidized lignophenol ELP1 was prepared through synthesis by the procedure of Example 1, except for using a lignophenol and an aqueous calcium carbonate solution having a pH of 11.8. ELP1 was prepared in a yield of 102 grams, had a weight-average molecular weight Mw' of 7600, and was soluble in 2MOE. The introduction of epoxy groups into lignophenol was confirmed through $^1$H-NMR and FT-IR analyses.

COMPARATIVE EXAMPLE 1

In a 2-liter four-neck flask equipped with stirring blades, a condenser and a thermometer were placed 100 grams of a low-molecular-weight lignin and 300 grams of a 10% aqueous sodium hydroxide solution, followed by stirring for 30 minutes to give a solution.

The solution was further combined with 300 grams of epichlorohydrin, followed by heating under reflux at 92° C. for one hour.

The reaction mixture was cooled to room temperature, placed in a separating funnel, and washed with pure water until the oil layer became neutral. After removing water therefrom, the residue was combined with 30 grams of a 10% aqueous sodium hydroxide solution and reacted at 92° C. for one hour, followed by refluxing and washing with water. After removing about 800 of epichlorohydrin, water and by-products, the residue was placed in 2 liters of ethanol to give white precipitates.

The precipitates were collected by filtration, dried in vacuo, and thereby yielded an epoxidized lignin ELh1. The introduction of epoxy groups in ELh1 was confirmed through $^1$H-NMR and FT-IR analyses. The epoxidized lignin ELh1 was prepared in a yield of 106 grams, but its weight-average molecular weight Mw' could not be measured, because it was insoluble in tetrahydrofuran or N,N-dimethylformamide used as a solvent for gel permeation chromatography (GPC). This was also insoluble in 2MOE. The 10% aqueous sodium hydroxide solution has a pH of 14.0.

COMPARATIVE EXAMPLE 2

An epoxidized lignin ELh2 was prepared by carrying out epoxidation under the same conditions as in Comparative Example 1, except for carrying out a reaction for the introduction of epoxy groups (epoxidation) at 45° C. and a pressure of 95 mmHg for half an hour (0.5 hour). The introduction of epoxy groups in ELh2 was confirmed through $^1$H-NMR and FT-IR analyses. ELh2 was prepared in a yield of 105 grams, but its weight-average molecular weight Mw' could not be measured, because it was insoluble in tetrahydrofuran or N,N-dimethylformamide. This was also insoluble in 2MOE.

COMPARATIVE EXAMPLE 3

An epoxidized lignophenol ELPh3 was prepared by carrying out epoxidation under the same conditions as in Comparative Example 2, except for using a lignophenol as the biomass compound. The introduction of epoxy groups in ELPh3 was confirmed through $^1$H-NMR and FT-IR analyses. ELPh3 was prepared in a yield of 106 grams, but its weight-average molecular weight Mw' could not be measured, because it was insoluble in tetrahydrofuran or N,N-dimethylformamide. This was also insoluble in 2MOE.

COMPARATIVE EXAMPLE 4

An epoxidized lignin ELh4 was prepared by the procedure of Comparative Example 1, except for using a low-molecular-weight lignin and an aqueous sodium carbonate solution having a pH of 10.9, and carrying out an epoxidation reaction at 92° C. for 2 hours. ELh4 was prepared in a yield of 106 grams and had a weight-average molecular weight Mw' of 1600. ELh4 was soluble in 2MOE, but the introduction of epoxy groups thereinto was not confirmed by $^1$H-NMR and FT-IR analyses.

The data obtained in Examples 1 to 4 and Comparative Examples 1 to 4 demonstrate that, when low-molecular-weight lignins and lignophenols are used as raw-material biomass-derived compounds, the weight-average molecular weights Mw' of the resulting epoxy compounds fall within twice the weight-average molecular weights Mw of the raw materials, and the product epoxy compounds show less increase in molecular weight and excel in solubility, when prepared by using an aqueous alkali solution having a pH ranging from 13.5 to 11.0.

In Comparative Examples 1 to 3 using an aqueous sodium hydroxide solution having a pH of 14.0, the epoxidation of the prepared products was confirmed through $^1$H-NMR and FT-IR analyses, but their weight-average molecular weights Mw' could not be measured, because they were insoluble in N,N-dimethylformamide or tetrahydrofuran. This is probably because the products gained higher molecular weights and partially underwent a crosslinking reaction during the epoxidation reaction.

In Comparative Example 4 using a weakly alkaline aqueous sodium carbonate solution having a pH of 10.9, the product showed good solubility but the introduction of epoxy groups (epoxidation) was not confirmed through $^1$H-NMR, indicating that epoxidation was insufficient.

Next, the prepared products were formulated into varnishes, copper-clad laminates were prepared using the varnishes, and properties of the copper-clad laminates were tested.

EXAMPLES 5 TO 11

Properties of Copper-Clad Laminates Prepared Using Varnishes of Epoxy Resin Compositions In Example 5, a varnish of epoxy resin composition was prepared by adding a stoichiometric amount of a low-molecular-weight lignin as a curing agent to the epoxidized lignin EL1, where EL1 was prepared in Example 1, had a weight-average molecular weight Mw' of 2800 and had an epoxy equivalent of 395 g/eq; further adding 0.5 percent by weight of P-200 (catalyst) relative to the amount of the epoxy resin composition; and adding a 1:1 (by weight) solvent mixture of 2-methoxyethanol and methyl ethyl ketone so as to give a resin concentration of 50 percent by weight.

In Examples 6 to 11, varnishes were prepared by the procedure of Example 5, except for using components such as epoxy compound, curing agent, and curing catalyst given in Table 1. As the organic solvent, the solvent mixture as with Example 5 was used.

Glass clothes each 30-cm square and 100 μm thick were impregnated with each varnish of epoxy resin composition, heated in a hot-air oven at 130° C. for eight minutes so as to allow the epoxy resin composition to be in an intermediate curing stage (B-stage), and thereby yielded six plies of non-sticky prepregs. The six plies were laid on one another to give a laminate, the laminate was sandwiched between two plies of copper foil each 35 μm thick, heated using a vacuum press at a heating rate of 6° C. per minute to 220° C., further held at 220° C. for one hour for complete curing (C-stage), and thereby yielded copper-clad laminates without defects.

The compositions and properties of the copper-clad laminates prepared in Examples 5 to 11 are shown in Table 1, in which the abbreviation "828" refers to "JER 828".

COMPARATIVE EXAMPLE 5

The resin composition according to Comparative Example 5 also given in Table 1 could not be formulated into a varnish, and a layer formed from the resin composition used as intact in the test for resistance to soldering heat was peeled off due to its low peel strength.

TABLE 1

Properties of Epoxy Resin Composition Varnishes and Copper-clad Laminates

| Number | Epoxy compound | Curing agent | Curing catalyst (0.5 percent by weight) | Solubility* | Tg (° C.) | Peel strength | Resistance to soldering heat |
|---|---|---|---|---|---|---|---|
| Example 5 | EL1 | Low-molecular lignin | P-200 | Good | 220 | 1.4 | Good |
| Example 6 | EL2 | Low-molecular lignin and MHAC-P | P-200 | Good | 245 | 1.3 | Good |
| Example 7 | EL3 | HP 850 | P-200 | Good | 260 | 1.4 | Good |
| Example 8 | EL1 and 828 | KAYAHARD AA | none | Good | 230 | 1.3 | Good |
| Example 9 | ELP1 | LP | P-200 | Good | 240 | 1.4 | Good |
| Example 10 | ELP1 | LP and HP 850 | P-200 | Good | 225 | 1.4 | Good |
| Example 11 | ELP1 and 828 | none | P-200 | Good | 200 | 1.2 | Good |
| Comparative Example 5 | ELPh3 | HP 850 | P-200 | Poor | 180 | 0.6 | Poor |

*1:1 (by weight) mixture of 2-methoxyethanol and methyl ethyl ketone
LP: Lignophenol

EXAMPLE 12

(Resin Encapsulants)

A series of resin encapsulants were prepared by kneading epoxy resin compositions using a three-roll mill and a vacuum masher. Their compositions are as follows.

Initially, 45 grams of RE 404S (bisphenol-F epoxy resin; supplied by Nippon Kayaku Co., Ltd., having an epoxy equivalent of 165 g/eq), 55 grams of ELL and 120 grams of a lignin were mixed, and the mixture was further combined with 0.5 percent by weight of the catalyst P-200 and 2 percent by weight of the coupling agent KBM 403 relative to the total amount of the epoxy resin composition.

The mixture was further combined with 1.0 percent by weight of an ion trapper (ion scavenger) IWE 500 (supplied by Toagosei Co., Ltd.) and thereby yielded an epoxy resin composition A.

Next, three types of high-purity spherical fillers were mixed, the mixture was added in an amount of 50 percent by volume to the epoxy resin composition A and thereby yielded a resin encapsulant A. The three types of high-purity spherical fillers were SP-4B (supplied by Fuso Chemical Co., Ltd., having an average particle diameter of 5.1 μm), QS4F2 (supplied by Mitsubishi Rayon Co., Ltd., having an average particle diameter of 4.6 μm), and SO25R (supplied by Tatsumori Ltd., having an average particle diameter of 0.68 μm).

The resin encapsulant A had a glass transition temperature Tg of 180° C. and a shear strength of 8.8 MPa.

A resin encapsulant B was prepared by the procedure as in the resin encapsulant A, except for forming a resin composition using 55 grams of RE 4045 and 59 grams of MHAC-P.

The resin encapsulant B had a glass transition temperature Tg of 170° C. and a shear strength of 3.8 MPa, which properties are inferior to those of the resin encapsulant A. This is probably because the resin encapsulant A gives a cured product containing a larger amount of hydroxyl groups derived from the material biomass compound.

The resin encapsulant A was applied to a flip-chip ball grid array (FC-BGA) illustrated in FIG. 1.

In FIG. 1, the reference numerals "1" stands for a wiring circuit board, "2" stands for a gold plating, "3" stands for a gold bump (solder bump), "4" stands for a semiconductor device, "5" stands for a solder ball, and "6" stands for a resin encapsulant. The gold plating 2 of the wiring circuit board 1 and the semiconductor device 4 are coupled to each other through the gold bump 3. A gap between the wiring circuit board 1 and the semiconductor device 4 was sealed by applying the resin encapsulant 6 thereto and heating the applied resin encapsulant at 180° C. according to the capillary flow method. The gap was 100 μm and the pitch between bumps (intervals between the adjacent gold bumps 3) was 150 μm.

In this way, the resin encapsulant A was verified to be applicable to FC-BGA.

As a result of comparisons between the examples and comparative examples, the biomass-derived epoxy resins according to the present invention have both high glass transition temperatures (Tg: heat resistance properties) and satisfactory solubility in organic solvents. In addition, they have higher shear strengths than those of the known equivalents.

What is claimed is:

1. A method for manufacturing a biomass-derived epoxy compound, comprising the steps of:
    dissolving a raw-material biomass-derived compound in an aqueous alkali solution, the raw-material biomass-derived compound containing at least a hydroxy group;
    adding epichlorohydrin to the solution and heating the resulting mixture to a temperature sufficient to epoxidize the raw-material biomass-derived compound;
    evaporating unreacted epichlorohydrin, water, and by-products from the mixture, yielding a residue containing a biomass-derived epoxy compound;
    combining the residue with an alcohol; and
    precipitating the biomass-derived epoxy compound,
    wherein the aqueous alkali solution has a pH of 13.5 to 11.0.

2. The method for manufacturing a biomass-derived epoxy compound according to claim 1, wherein the aqueous alkali solution is at least one selected from the group consisting of aqueous organic ammonium solutions, aqueous alkaline earth metal salt solutions, and aqueous carbonate solutions.

3. The method for manufacturing a biomass-derived epoxy compound according to claim 1, wherein the raw-material biomass-derived compound has a weight-average molecular weight of 300 to 10,000.

4. The method for manufacturing a biomass-derived epoxy compound according to claim 1, wherein the raw-material biomass-derived compound is at least one selected from the group consisting of lignins and lignophenols.

* * * * *